(12) United States Patent
Chen et al.

(10) Patent No.: US 9,539,011 B2
(45) Date of Patent: Jan. 10, 2017

(54) VASO-OCCLUSIVE DEVICE DELIVERY SYSTEM

(71) Applicants: STRYKER CORPORATION, Kalamazoo, MI (US); STRYKER NV OPERATIONS LIMITED, Dublin (IE)

(72) Inventors: Hancun Chen, San Ramon, CA (US); Clifford Teoh, Los Altos, CA (US); Lantao Guo, San Ramon, CA (US); Timothy Odell, Fremont, CA (US); Richard Murphy, Sunnyvale, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 330 days.

(21) Appl. No.: 14/206,371

(22) Filed: Mar. 12, 2014

(65) Prior Publication Data
US 2014/0277094 A1    Sep. 18, 2014

Related U.S. Application Data

(60) Provisional application No. 61/785,148, filed on Mar. 14, 2013.

(51) Int. Cl.
A61B 17/12    (2006.01)

(52) U.S. Cl.
CPC ..... A61B 17/1214 (2013.01); A61B 17/12022 (2013.01); A61B 2017/12068 (2013.01)

(58) Field of Classification Search
CPC ................ A61B 17/12022; A61B 17/12027; A61B 17/12031; A61B 17/1204; A61B 17/1205; A61B 17/12109; A61B 17/12113; A61B 17/1214; A61B 17/12145;A61B 17/12154; A61B 2017/12054–2017/12072; A61B 17/12077; A61B 2017/1209
See application file for complete search history.

(56) References Cited

U.S. PATENT DOCUMENTS 4,994,069 A     2/1991  Ritchart et al.
2002/0099408 A1*  7/2002  Marks .............. A61B 17/12022
                                                    606/200

(Continued)

FOREIGN PATENT DOCUMENTS

EP      2006024040 A2    3/2006
EP         1884208 A1    2/2008
WO         0158366 A1    8/2001

OTHER PUBLICATIONS

PCT International Search Report and Written Opinion for PCT/US2014/024399, Applicant Stryker Corporation, Forms PCT/ISA/210, 220, and 237, dated Sep. 8, 2014, (14 pages).

*Primary Examiner* — David C Eastwood
(74) *Attorney, Agent, or Firm* — Vista IP Law Group LLP

(57) ABSTRACT

A vaso-occlusive device delivery assembly includes a pusher assembly having a proximal end, a distal end, and a pusher lumen extending therebetween; a vaso-occlusive device; and a tubular member mechanically connecting the pusher assembly to the vaso-occlusive device, the tubular member having a proximal end, a distal end, a tube lumen extending therebetween, and a detach zone, wherein the proximal end of the tubular member extends into the pusher assembly lumen at the distal end of the pusher assembly. A heat generating member is disposed in the tube lumen, such that, when activated, the heat generating member generates heat that melts or otherwise thermally degrades the tubular member at the detach zone, thereby detaching the vaso-occlusive device from the pusher assembly.

19 Claims, 9 Drawing Sheets

(56) References Cited

U.S. PATENT DOCUMENTS

| | | | |
|---|---|---|---|
| 2006/0052815 A1* | 3/2006 | Fitz | A61B 17/0057 |
| | | | 606/200 |
| 2006/0135986 A1* | 6/2006 | Wallace | A61B 17/12113 |
| | | | 606/200 |
| 2007/0239192 A1* | 10/2007 | Litzenberg | A61B 17/12022 |
| | | | 606/191 |
| 2007/0239196 A1* | 10/2007 | Pomeranz | A61B 17/12022 |
| | | | 606/191 |
| 2010/0114085 A1* | 5/2010 | Thompson | A61B 18/08 |
| | | | 606/29 |
| 2013/0261656 A1* | 10/2013 | Lorenzo | A61B 17/12154 |
| | | | 606/200 |

* cited by examiner

VASO-OCCLUSIVE DEVICE DELIVERY SYSTEM

RELATED APPLICATION DATA

The present application claims the benefit under 35 U.S.C. §119 to U.S. Provisional Application Ser. No. 61/785,148, filed Mar. 14, 2013. The foregoing application is hereby incorporated by reference into the present application in its entirety.

FIELD

The field of the disclosed inventions generally relates to systems and delivery devices for implanting vaso-occlusive devices for establishing an embolus or vascular occlusion in a vessel of a human or veterinary patient. More particularly, the disclosed inventions relate to heat actuated vaso-occlusive device delivery systems.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" wire is then passed through the micro-catheter, until a vaso-occlusive device coupled to a distal end of the pusher assembly is extended out of the distal end opening of the micro-catheter and into the aneurysm. Once in the aneurysm, segments of some vaso-occlusive devices break off to allow more efficient and complete packing. The vaso-occlusive device is then released or "detached" from the end of the pusher assembly, and the pusher assembly is withdrawn back through the catheter. Depending on the particular needs of the patient, one or more additional occlusive devices may be pushed through the catheter and released at the same site.

One well-known way to release a vaso-occlusive device from the end of the pusher assembly is through the use of an electrolytically severable junction, which is a small exposed section or detachment zone located along a distal end portion of the pusher assembly. The detachment zone is typically made of stainless steel and is located just proximal of the vaso-occlusive device. An electrolytically severable junction is susceptible to electrolysis and disintegrates when the pusher assembly is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher completes an electrolytic detachment circuit with a return electrode, and the detachment zone disintegrates due to electrolysis.

While electrolytically severable junctions have performed well, there remains a need for other systems and methods for delivery vaso-occlusive devices into vessel lumens.

SUMMARY

In one embodiment of the disclosed inventions, a vaso-occlusive device delivery assembly includes a pusher assembly having a proximal end, a distal end, and a pusher lumen extending therebetween. The assembly further includes a tubular member mechanically connecting the pusher assembly to a vaso-occlusive device, the tubular member having a proximal end, a distal end, a tube lumen extending therebetween, and a detach zone. The proximal end of the tubular member extends into the pusher assembly lumen at the distal end of the pusher assembly. A heat generating member is disposed in the tube lumen, such that, when activated, the heat generating member generates heat that melts or otherwise thermally degrades the tubular member at the detach zone, thereby detaching the vaso-occlusive device from the pusher assembly.

In some embodiments, the pusher assembly also includes first and second conductors extending between the proximal and distal ends of the pusher assembly, the heat generating member is a resistive heater coil electrically connected to the respective first and second conductors to form an electrical circuit, and the heat generating member is activated by applying a current therethrough. A pitch of a proximal portion of the heater coil may be greater than a pitch of a distal portion of the heater coil, such that the heater coil has a non-uniform heat distribution. Additionally, material may be added as a heat sink to focus higher temperatures at the detachment zone while absorbing heat to lower temperatures at the connections to the pusher assembly and/or vaso-occlusive coil. The heat may alternately be generated using current applied at a radio frequency. The detach zone may be treated, e.g., thermally, chemically, radioactively, or mechanically weakened, to accelerate detachment of the vaso-occlusive device from the pusher assembly. The longitudinal cross section of the material may also be varied to focus detachment in a specific region. The transverse section can have a shape other than round.

In some embodiments, the vaso-occlusive device delivery assembly also includes an elongate body disposed in the tube lumen at the distal end of the tubular member, where a distal portion of the tubular member is attached (e.g., heat-shrunk) to an outer surface of the elongate body, thereby increasing a tension on the detach zone to accelerate detachment of the vaso-occlusive device from the pusher assembly. The vaso-occlusive device delivery assembly of claim 1 may also include a locking coil disposed in the tube lumen at the distal end of the tubular member, where both the locking coil and the distal end of the tubular member are disposed in a lumen of the vaso-occlusive device, and the locking coil sized so as to increase an interference fit between the tubular member and the vaso-occlusive device.

In some embodiments, the pusher assembly also includes a cylindrical body disposed around and thermally insulating the detach zone. The cylindrical body may be configured to increase an axial columnar strength of the vaso-occlusive device delivery assembly.

In some embodiments, the tubular member includes a radially enlarged distal portion, and a proximal end of the vaso-occlusive device is secured to the tubular member by an interference fit within the radially enlarged distal portion of the tubular member. The proximal end of the tubular member may be connected to the pusher assembly by a first adhesive connection and the distal end of the tubular member may be connected to the vaso-occlusive device by a second adhesive connection. The vaso-occlusive device delivery assembly may also include proximal and distal seals attached to the respective proximal and distal ends of the tubular member, and forming respective seals therewith, such that the tube lumen is sealed.

In some embodiments, the vaso-occlusive device including a stretch-resisting member having a distal end secured to a distal portion of the vaso-occlusive device, and a proximal end secured to an adapter disposed in a proximal end portion of a lumen of the vaso-occlusive device, where the adapter includes a flattened body defining an opening in the distal end thereof, and where the stretch-resisting member forms a loop passing through the opening, thereby attaching the stretch-resisting member to the adapter. In similar embodiments, the adapter includes a coil, and the stretch-resisting member forms a loop passing through an open winding in the distal end of the coil, thereby attaching the stretch-resisting member to the adapter.

In some embodiments, the heat generating member is configured to heat air within the pusher lumen to thereby increase a pressure therein to accelerate detachment of the vaso-occlusive device from the pusher assembly. The heat generating member may include carbon. The tubular member may include a polymer, which may be high-density polyethylene, low-density polyethylene, polypropylene, polyethylene terephthalate, and polycaprolactone. The polymers may contain additives, such as glass or metal fibers, to increase strength. The fibers may also enhance the detachment by reducing the rate of heat conduction or increasing it. The polymer may also be in a stressed state such that the application of heat causes not only separation but also causes the two ends to shrink away from one another.

In some embodiments, the tubular member includes a plurality of concentric layers. In those embodiments, the tubular member may include a low melting point inner layer and a high melting point outer layer.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
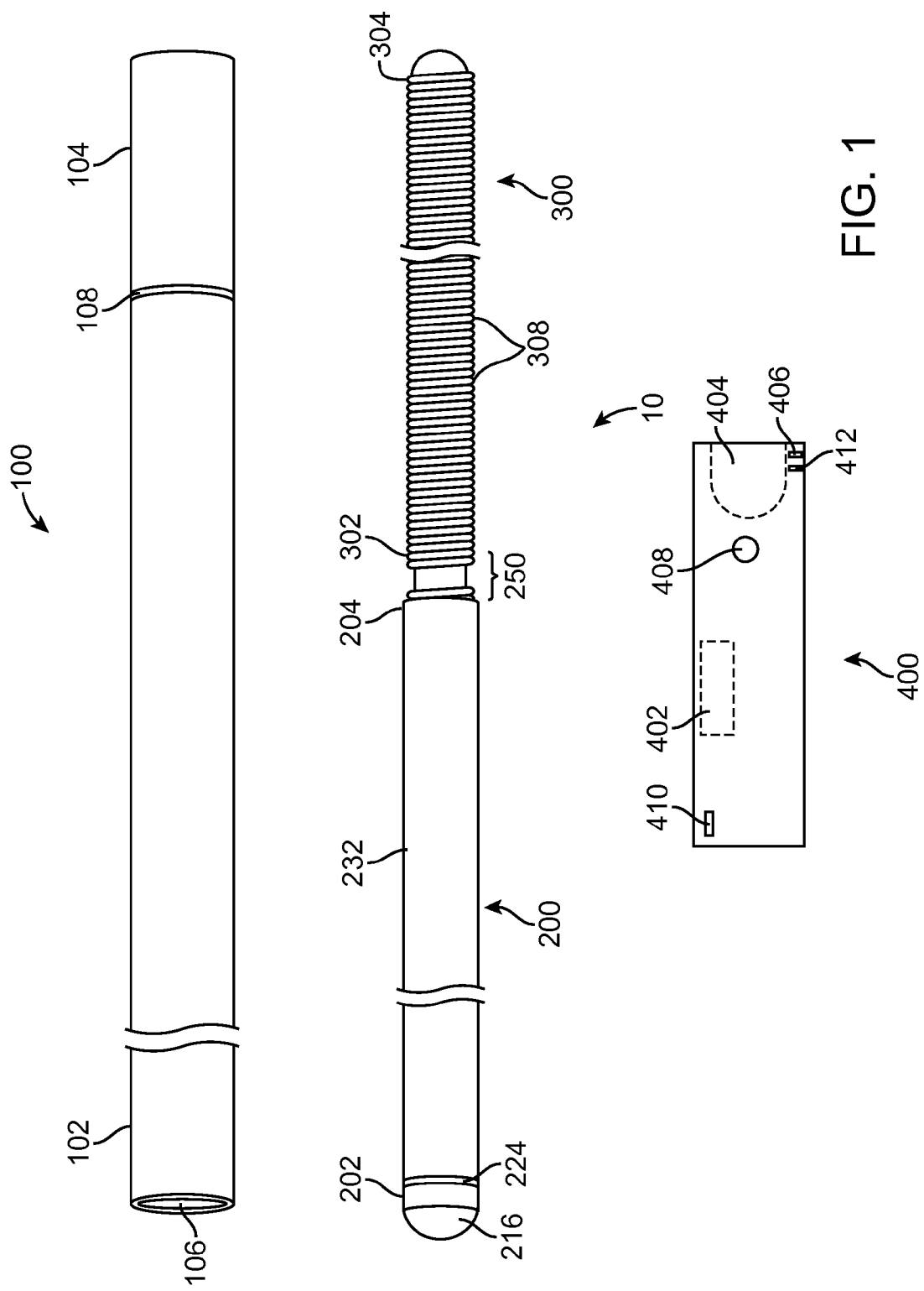
FIG. 1 is a schematic view of a vaso-occlusive device delivery system, according to one embodiment of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 illustrates a known vaso-occlusive device delivery system 10. In the system 10 illustrated in FIG. 1, the vaso-occlusive device is a vaso-occlusive coil 300. The system 10 includes a number of subcomponents or subsystems. These include a delivery catheter 100, a pusher assembly 200, a vaso-occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the pusher assembly 200 and the vaso-occlusive coil 300. Further, the lumen 106 is sized for the passage of a guidewire (not shown) which may optionally be used to properly guide the delivery catheter 100 to the appropriate delivery site.

The delivery catheter 100 may include a braided-shaft construction of stainless steel flat wire that is encapsulated or surrounded by a polymer coating. By way of non-limiting example, HYDROLENE® is a polymer coating that may be used to cover the exterior portion of the delivery catheter 100. Of course, the system 10 is not limited to a particular construction or type of delivery catheter 100 and other constructions known to those skilled in the art may be used for the delivery catheter 100. The inner lumen 106 may be advantageously coated with a lubricious coating such as PTFE to reduce frictional forces between the delivery catheter 100 and the respective pusher assembly 200 and vaso-occlusive coil 300 being moved axially within the lumen 106. The delivery catheter 100 may include one or more optional marker bands 108 formed from a radiopaque material that can be used to identify the location of the delivery catheter 100 within the patient's vasculature system using imaging technology (e.g., fluoroscope imaging). The length of the delivery catheter 100 may vary depending on the particular application, but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 104 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the respective pusher assembly 200 and vaso-occlusive coil 300, but generally the OD of the lumen 106 of the delivery catheter 100 (I.D. of delivery catheter 100) is less than about 0.02 inches. The delivery catheter 100 is known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Figure 3:
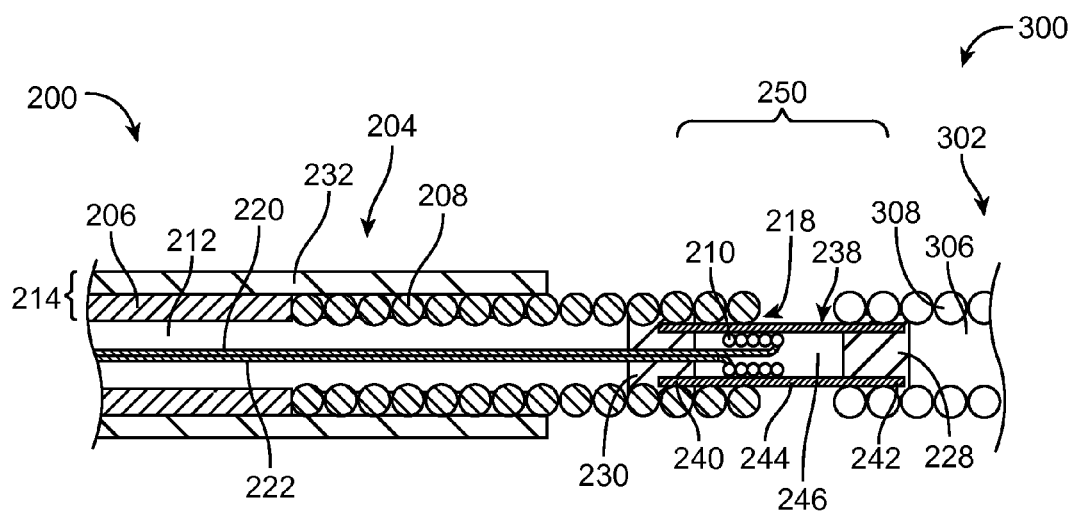
FIGS. 3-12 are detailed longitudinal cross-sectional views of vaso-occlusive device delivery systems according to various embodiments of the disclosed inventions, which depict the junction between the various pusher assemblies and vaso-occlusive devices.

As illustrated in FIGS. 1 and 3, the system 10 includes a pusher assembly 200 configured for axial movement within the lumen 106 of the delivery catheter 100. The pusher assembly 200 generally includes a proximal end 202 and a distal end 204. The pusher assembly 200 includes a pusher conduit 214, which has a proximal tubular portion 206 and a distal coil portion 208, and defines a pusher lumen 212 and a distal opening 218 in communication with the pusher lumen 212.

FIG. 3 illustrates a detailed longitudinal cross-sectional view of the junction 250 between the pusher assembly 200 and the vaso-occlusive coil 300 according to one embodiment of the disclosed inventions. Similar elements of this embodiment are identified with the same reference numbers as discussed above with respect to FIG. 1. The pusher assembly 200 includes a proximal end 202 and a distal end 204 and measures between around 184 cm to around 186 cm in length. The proximal tubular portion 206 may be formed from, for example, a flexible stainless steel hypotube. The proximal tubular portion 206 may be formed from stainless steel hypotube having an OD of 0.01325 inches and inner diameter (ID) of 0.0075 inches. The length of the hypotube section may be between around 140 cm to around 150 cm, although other lengths may also be used.

A distal coil portion 208 is joined in end-to-end fashion to the distal face of the proximal tubular portion 206. The joining may be accomplished using a weld or other bond. The distal coil portion 208 may have a length of around 39 cm to around 41 cm in length. The distal coil portion 208 may comprise a coil of 0.0025 inches×0.006 inches. The first dimension generally refers to the OD of the coil wire that forms the coil. The latter dimension generally refers to the internal mandrel used to wind the coil wire around to form the plurality of coil winds and is the nominal ID of the coil. One or more windings of the distal coil portion 208 may be formed from a radiopaque material, forming marker coils. For example, the distal coil portion 208 may include a segment of stainless steel coil (e.g., 3 cm in length), followed by a segment of platinum coil (which is radiopaque and also 3 mm in length), followed by a segment of stainless steel coil (e.g., 37 cm in length), and so on and so forth.

An outer sleeve 232 or jacket surrounds a portion of the proximal tubular portion 206 and a portion of the distal coil portion 208 of the pusher conduit 214. Although the outer sleeve 232 depicted in FIG. 3 does not extend to the distal terminal end of the pusher assembly 200, in other embodiments the outer sleeve 232 can extend to the distal terminal end and distally beyond. The outer sleeve 232 covers the interface or joint formed between the proximal tubular portion 206 and the distal coil portion 208. The outer sleeve 232 may have a length of around 50 cm to around 54 cm. The outer sleeve 232 may be formed from a polyether block amide plastic material (e.g., PEBAX 7233 lamination). The outer sleeve 232 may include a lamination of PEBAX and HYDROLENE® that may be heat laminated to the pusher assembly 200. The OD of the outer sleeve 232 may be less than 0.02 inches and advantageously less than 0.015 inches. In embodiments where the pusher conduit 214 forms the negative conductor 222, the outer sleeve 232 is removed from the very distal end of the pusher conduit 214, during manufacturing, to form an exposed negative electrical contact 224.

As shown in FIG. 3, the system 10 also includes a tubular member 238 that detachably connects (i.e., releasably attaches) the vaso-occlusive coil 300 to the pusher assembly 200. The tubular member 238 has a proximal end 240 and a distal end 242, both of which are open, and a tube lumen 246 therebetween. The tubular member 238 may be made from biocompatible, heat degradable polymers with low melting points such as high-density polyethylene, low-density polyethylene, polypropylene, polyethylene terephthalate, and polycaprolactone.

The proximal end 240 of the tubular member 238 is disposed in the distal end of the pusher lumen 212. The open proximal end 240 of the tubular member 238 is attached to the pusher assembly 200 by a proximal seal 230, effectively closing the proximal end 240 of the tubular member 238. The proximal seal 230 is also attached to the interior surface of the pusher conduit 214 in the pusher lumen 212. The positive and negative conductors 220, 222 extend through the proximal seal 230 while the proximal seal 230 maintains a substantially fluid tight seal between regions proximal and distal of the proximal seal 230. The distal end 242 of the tubular member 238 is attached to the vaso-occlusive coil 300 in the proximal end of the vaso-occlusive coil lumen 306 by a distal seal 228. The proximal and distal seals 230, 228 may be formed from an adhesive.

The system 10 further includes a heat generating member 210 disposed in the tube lumen 246, between the proximal and distal seals 230, 228. The tubular member 238 insulates the environment external to the tubular member 238 from heat generated by the heat generating member 210. In the embodiment depicted in FIG. 3, the heat generating member 210 is a resistive heating coil 210 disposed in the distal end 204 of the pusher assembly 200. In other embodiments, the heat generating member 210 may include mechanical, inductive, magnetic, or optical mechanisms.

The resistive heating coil 210 is connected to positive and negative conductors 220, 222 disposed in the pusher lumen 212. The resistive heating coil 210 can be wound from platinum or Nichrome® (nickel chromium alloy) wire, such that when a current is delivered through the resistive heating coil 210 by the positive and negative conductors 220, 222 from the power supply 400, a resistance to the current flow generates heat in the resistive heating coil 210. The heating coil 210 can also be wound from carbon fibers. The resistive heating coil 210 may also have a variable pitch with a distal portion having a lesser pitch (more windings per unit length) than a proximal portion. A heating coil 210 with variable pitch would have non-uniform heat distribution with more heat at the distal and to accelerate melting or thermal degradation of the tubular member 238.

The positive and negative conductors 220, 222 may be formed from an electrically conductive material such as twisted copper wire coated with polyimide, with an OD of around 0.00175 inches. The proximal ends of the positive and negative conductors 220, 222 are electrically connected to positive and negative electrical contacts 216, 224, respectively. As shown in FIG. 1, positive and negative electrical contacts 216, 224 are located at the proximal end of the pusher assembly 200. The positive electrical contact 216 may be formed from a metallic solder (e.g., gold) that is configured to interface with a corresponding electrical contact (not shown) in the power supply 400 (described below). The negative electrical contact 224 may be an annular ring electrode disposed on top of an electrically insulative outer sleeve 232 at the proximal end of the pusher conduit 214 (described below). The positive and negative conductors 220, 222 may be coated with an insulative coating such as polyimide except where they connect to the positive and negative electrical contacts 216, 224, respectively.

Due to the proximity of the heating coil 210 to the tubular member 238 and the low melting point of the tubular member 238, when current is delivered through the heating coil 210 by the positive and negative conductors 220, 222, heat generated at the heating coil 210 melts or otherwise thermally degrades the tubular member 238, thereby detaching the vaso-occlusive coil 300 from the pusher assembly 200. This heat generated detachment is especially effective where, as in FIG. 3, the heating coil 210 is in contact with the tubular member 238.

Further, the tubular member 238 and the proximal and distal seals 230, 228 form a substantially fluid-tight chamber in the tube lumen 246. When the resistive heating coil 210 is activated as described above, wherein the fluid tight-chamber increases in temperature and pressure, facilitating bursting/severing the tubular member. This increase in pressure also pushes the detached vaso-occlusive coil 300 from the pusher assembly 200 with a positive thrust force. This pressure actuated detachment is described in co-owned application Ser. No. 61/785,556, filed Mar. 14, 2013, also entitled "Vaso-Occlusive Device Delivery System". The contents of the application Ser. No. 61/785,556 are fully incorporated herein by reference as though set forth in full.

Optionally, a detachment zone 244 between the proximal and distal ends 240, 242 of the tubular member 238 may be treated to facilitate severing of the tubular member 238. In the embodiment depicted in FIG. 4B, the detachment zone 244 is under tension. In other embodiments, the detachment zone 244 may be either thermally or mechanically (e.g., perforated) treated to facilitate detachment.

The vaso-occlusive coil 300 includes a proximal end 302, a distal end 304, and a lumen 306 extending there between. The vaso-occlusive coil 300 is made from a biocompatible metal such as platinum or a platinum alloy (e.g., platinum-tungsten alloy). The vaso-occlusive coil 300 includes a plurality of coil windings 308. The coil windings 308 are generally helical about a central axis disposed along the lumen 306 of the vaso-occlusive coil 300. The vaso-occlusive coil 300 may have a closed pitch configuration as illustrated in FIGS. 1 and 3. A tether (not shown), such as a suture, may extend from the proximal end 302 through the lumen 306 to the distal end 304 where it is connected to the distal end 304 of the vaso-occlusive coil 300.

Figure 2:
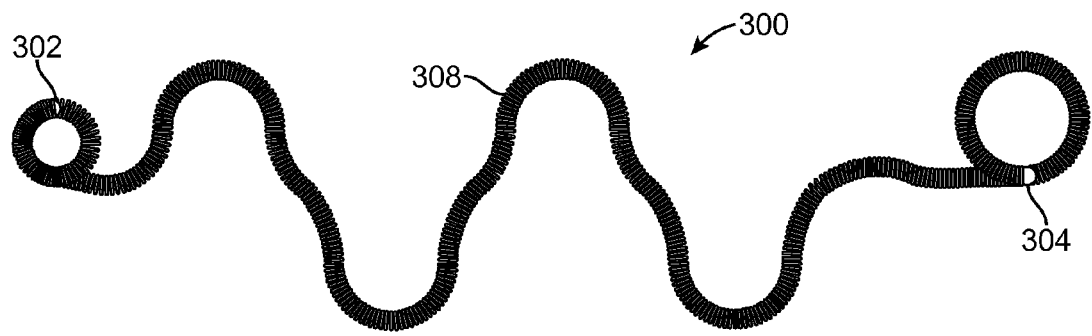
FIG. 2 is a side view of an occlusive coil in a natural state mode, illustrating one exemplary secondary configuration according to an embodiment of the disclosed inventions.

The vaso-occlusive coil 300 generally includes a straight configuration (as illustrated in FIG. 1) when the vaso-occlusive coil 300 is loaded within the delivery catheter 100. Upon release, the vaso-occlusive coil 300 generally takes a secondary shape which may include three-dimensional helical configurations. FIG. 2 illustrates one exemplary configuration of a vaso-occlusive coil 300 in a natural state. In the natural state, the vaso-occlusive coil 300 transforms from the straight configuration illustrated in, for instance, FIG. 1 into a secondary shape. The secondary shaped may include both two and three dimensional shapes of a wide variety. FIG. 2 is just one example of a secondary shape of a vaso-occlusive coil 300 and other shapes and configurations are contemplated to fall within the scope of the disclosed inventions. Also, the vaso-occlusive coil 300 may incorporate synthetic fibers (not shown) over all or a portion of the vaso-occlusive coil 300 as is known in the art. These fibers may be attached directly to coil windings 308 or the fibers may be integrated into the vaso-occlusive coil 300 using a weave or braided configuration. Of course, the system 10 described herein may be used with occlusive coils 300 or other occlusive structures having a variety of configurations, and is not limited to occlusive coils 300 having a certain size or configuration.

As shown in FIG. 1, the system 10 further includes a power supply 400 for supplying direct current to the positive and negative conductors 220, 222. Activation of the power supply 400 causes electrical current to flow in a circuit including the positive and negative conductors 220, 222 and the resistive heating coil 210. The power supply 400 preferably includes an onboard energy source, such as batteries (e.g., a pair of AAA batteries), along with drive circuitry 402. The drive circuitry 402 may include one or more microcontrollers or processors configured to output a driving current. The power supply 400 illustrated in FIG. 1 includes a receptacle 404 configured to receive and mate with the proximal end 202 of the delivery wire assembly 200. Upon insertion of the proximal end 202 into the receptacle 404, the positive, negative electrical contacts 216, 224 disposed on the delivery wire assembly 200 electrically couple with corresponding contacts (not shown) located in the power supply 400.

A visual indicator 406 (e.g., LED light) is used to indicate when the proximal end 202 of delivery wire assembly 200 has been properly inserted into the power supply 400. Another visual indicator 420 is activated if the onboard energy source needs to be recharged or replaced. The power supply 400 includes an activation trigger or button 408 that is depressed by the user to apply the electrical current to the resistive heating coil 210 via the positive and negative conductors 220, 222. Once the activation trigger 408 has been activated, the driver circuitry 402 automatically supplies current. The drive circuitry 402 typically operates by applying a substantially constant current, e.g., around 50-250 mA. A visual indicator 412 may indicate when the power supply 400 is supplying adequate current to the resistive heating coil 210.

In use, the vaso-occlusive coil 300 is attached to the pusher assembly 200 at junction 250. The attached vaso-occlusive coil 300 and pusher assembly 200 are threaded through the delivery catheter 100 to a target location (e.g., an aneurysm) in the patient's vasculature. Once the distal and 304 of the vaso-occlusive coil 300 reaches the target location, the vaso-occlusive coil 300 is pushed further distally until it's completely exits the distal and 104 of the delivery catheter 100.

In order to detach the vaso-occlusive coil 300 from the pusher assembly 200, the power supply 400 is activated by depressing the trigger 408. The drive circuitry 402 in the power supply 400 applies a current to the positive and negative conductors 220, 222 through the positive and negative electrical contacts 216, 224. As the applied current travels through the resistive heating coil 210, the resistive heating coil 210 generates heat. The generated heat raises the temperature of the tubular member 238 to its melting point, at which the tubular member 238 loses the structural integrity, becomes severed, and releases the vaso-occlusive coil 300 from the pusher assembly 200. After activation of the power supply 400, the vaso-occlusive coil 300 is typically detached in less than one second.

Further, the generated by the heating coil 210 increases the temperature and pressure of air in the substantially fluid-tight chamber facilitating severance of the tubular member to create and release of the vaso-occlusive coil 300 from the pusher assembly 200. Moreover, the vaso-occlusive coil 300 is ejected from the pusher assembly 200 by the increased pressure. This positive thrust force separating the vaso-occlusive coil 300 from the pusher assembly 200 ensures separation and prevents "sticky coils."

Figure 4A:
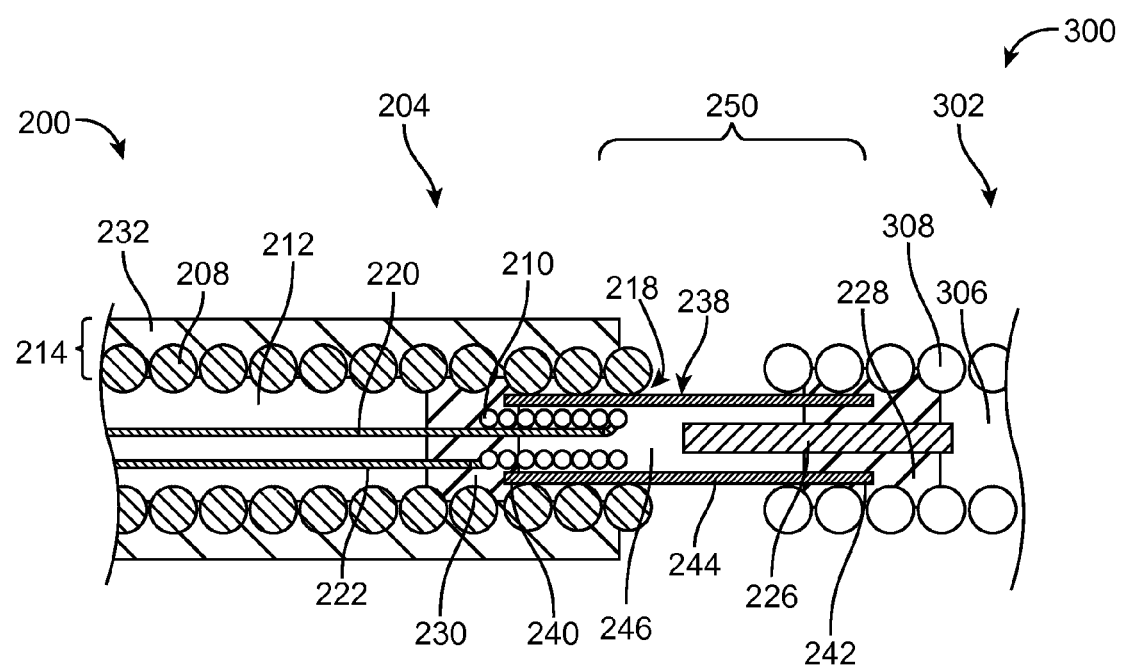
Figure 4B:
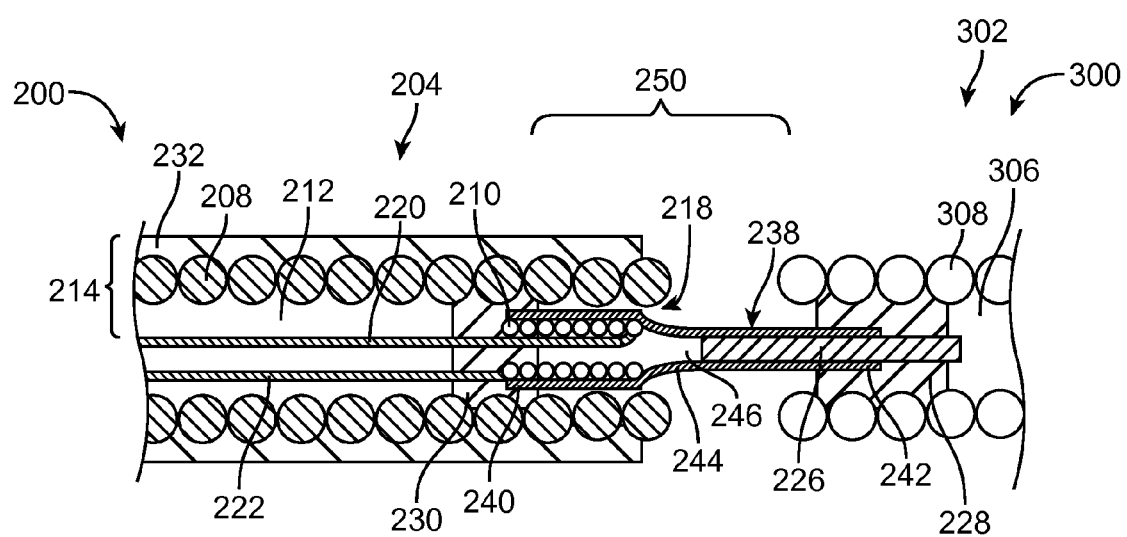

The vaso-occlusive device delivery system 10 depicted in FIGS. 4A and 4B is very similar to the system 10 depicted in FIG. 3. Similar elements of this embodiment are identified with the same reference numbers as discussed above with respect to FIG. 3. The difference between the systems 10 depicted in these figures is the addition of an elongate body/detach aid 226 in the tube lumen 246 at the distal end 242 of the tubular member 238 to the embodiment depicted in FIG. 3. The elongate body 226 is also secured to the distal seal 228. The tubular member 238 is heat-shrunk onto an outer surface of the elongate body 226 as shown in FIG. 4B. The heat-shrinking increases the tension in the tubular member 238, facilitating its severance and detach of the vaso-occlusive coil 300.

Figure 5:
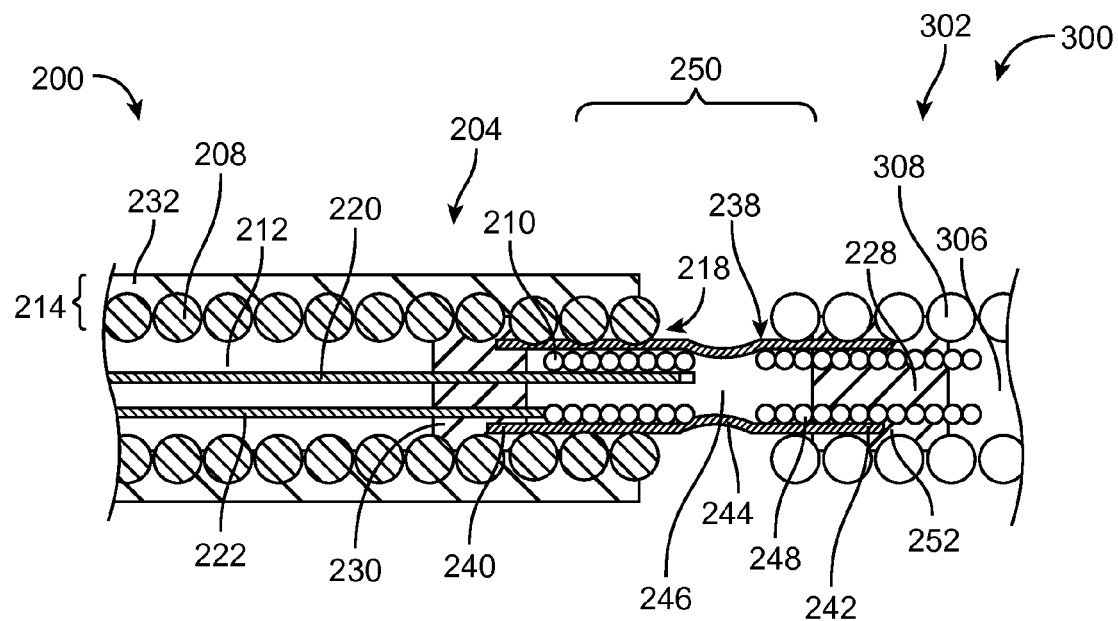

The vaso-occlusive device delivery system 10 depicted in FIG. 5 is also similar to the system 10 depicted in FIG. 3. Similar elements of this embodiment are identified with the same reference numbers as discussed above with respect to FIG. 3. The embodiment depicted in FIG. 5 has a modified detachment zone 244 and the addition of a locking coil 248. The detachment zone 244 of the tubular member 238 depicted in FIG. 5 has been weakened by heating and stretching to facilitate its severance and detach of the vaso-occlusive coil 300. The locking coil 248 is disposed in the tube lumen 246 at the distal end 242 of the tubular member 238. The OD of the locking coil 248 is slightly smaller than the ID of the vaso-occlusive coil 300. Accordingly the locking coil 248 and the vaso-occlusive coil 300 form an annular space 252 into which the distal end 242 of the tubular member 238 is secured with an interference fit.

Figure 6:
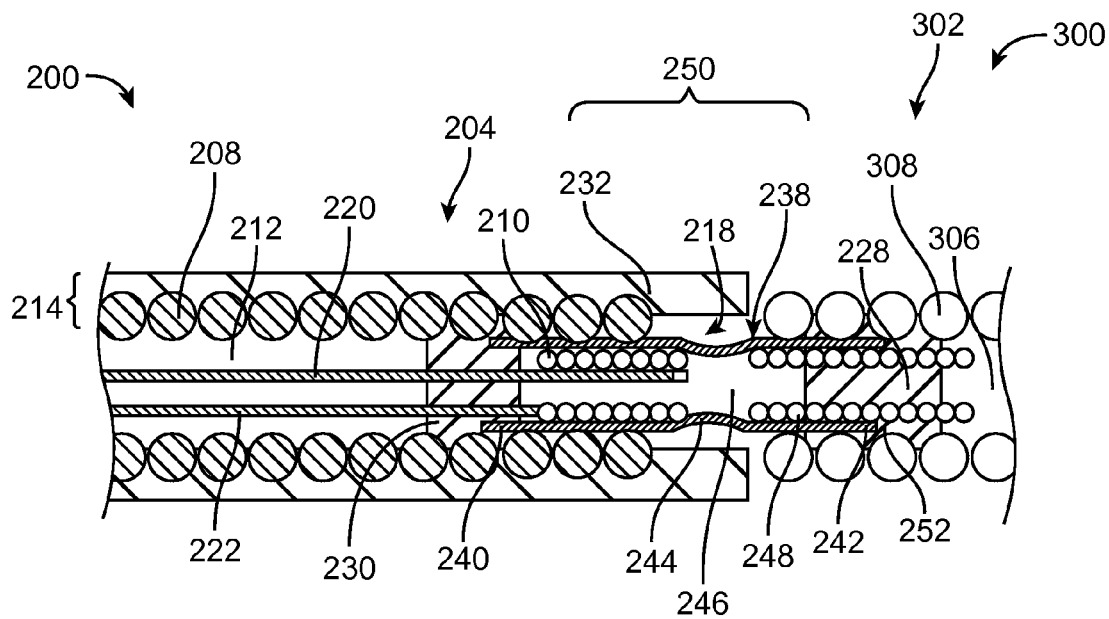

The embodiment depicted in FIG. 6 is very similar to the system 10 depicted in FIG. 5. Similar elements of this embodiment are identified with the same reference numbers as discussed above with respect to FIG. 5. In the embodiment depicted in FIG. 6, the outer sleeve 232 extends distally beyond the distal coil portion 208 of the pusher conduit 214, almost making contact with vaso-occlusive coil 300. The distal end of the outer sleeve 232 and the tubular member 238 further thermally insulates the heating coil 210 and the detachment zone 244. The distal end of the outer sleeve 232 simultaneously protects the environment external to the tubular member 238 from heat generated by the heat generating member 210 and increases heat apply to the detachment zone 244. The distal end of the outer sleeve 232 can also prevent polymer melt back and increase an axial columnar strength of the system 10.

Figure 7:
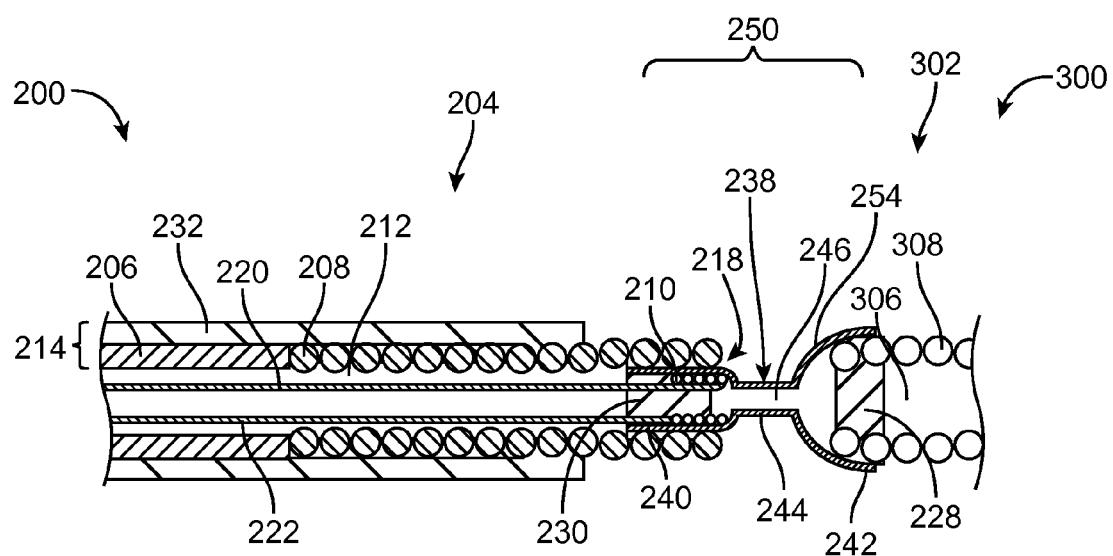

The vaso-occlusive device delivery system 10 depicted in FIG. 7 is also similar to the system 10 depicted in FIG. 3. Similar elements of this embodiment are identified with the same reference numbers as discussed above with respect to FIG. 3. The difference between the systems 10 depicted in these figures is that distal end 242 of the tubular member 238 includes a radially enlarged portion 254. The proximal end 302 of the vaso-occlusive coil 300 is secured to the tubular member 238 in the tube lumen 246 at the radially enlarged portion 254 by an interference fit. The proximal end 302 of the vaso-occlusive coil 300 can also be secured to the tubular member 238 with an adhesive.

Figure 8:
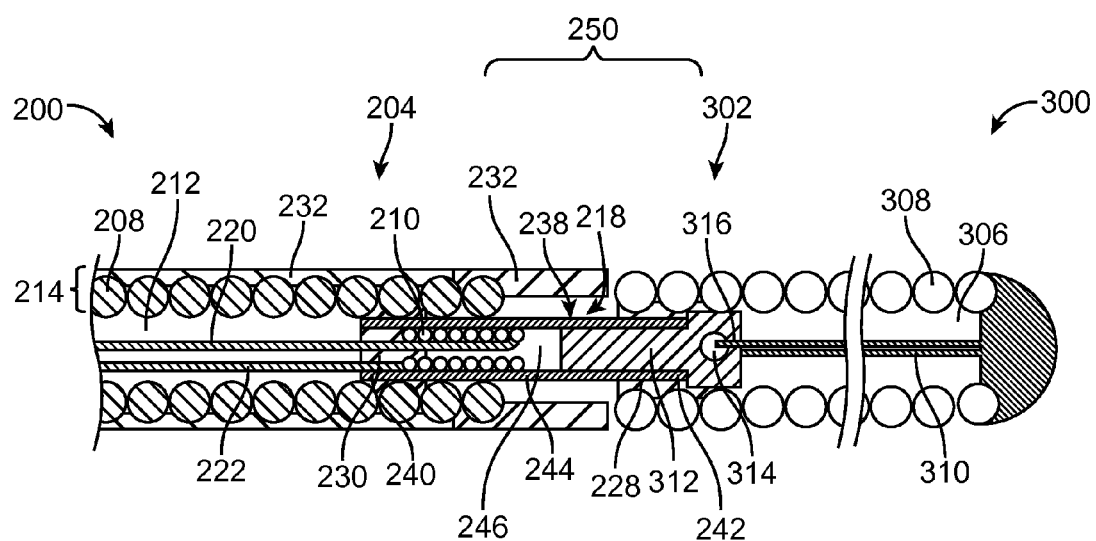

The vaso-occlusive device delivery system 10 depicted in FIG. 8 is similar to the systems 10 depicted in FIGS. 3 and 6. Similar elements of this embodiment are identified with the same reference numbers as discussed above with respect to FIGS. 3 and 6. Like the system 10 depicted in FIG. 6, the outer sleeve 232 of the pusher assembly 200 depicted in FIG. 8 extends distally beyond the distal coil portion 208 of the pusher conduit 214. The portion of the outer sleeve 232 that extends distally beyond the distal coil portion 208 of the pusher conduit 214 may be the same material as the remainder of the outer sleeve 232 or a different material. Further, the vaso-occlusive coil 300 depicted FIG. 8 has a stretch-resisting member 310 attached to the distal end 304 of vaso-occlusive coil 300. The vaso-occlusive coil 300 also includes an adapter 312 at least partially disposed in its lumen 306 at its proximal end 302. The adapter 312 is a flattened body defining an opening 314 at the distal end thereof. The proximal end of the stretch-resisting member 310 forms a loop 316 passing through the opening 314, thereby attaching the stretch-resisting member 310 to the adapter 312. The proximal end of the adapter 312 has a width approximately equal to the ID of the tubular member 238. Accordingly, when the proximal end of the adapter 312 is inserted into the tubular member 238, the tubular member 238 and the adapter 312 is attached by an interference fit. The tubular member 238 to also be attached to the vaso-occlusive coil 300 by an adhesive.

Figure 9:
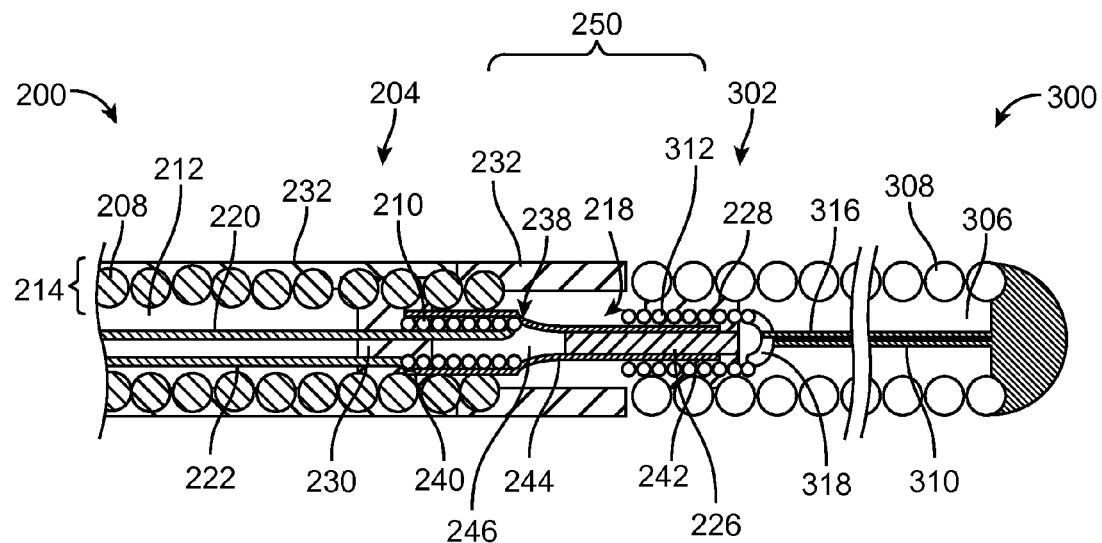

The vaso-occlusive device delivery system 10 depicted in FIG. 9 is similar to the systems 10 depicted in FIGS. 4B and 8. Similar elements of this embodiment are identified with the same reference numbers as discussed above with respect to FIGS. 4B and 8. Like the system 10 depicted in FIG. 4B, the tubular member 238 depicted in FIG. 9 is heat-shrunk onto an outer surface of an elongate body 226 disposed in the distal seal 228. Like the system 10 depicted in FIG. 8, the outer sleeve 232 of the pusher assembly 200 depicted in FIG. 9 extends distally beyond the distal coil portion 208 of the pusher conduit 214. Like the system 10 depicted in FIG. 8, the vaso-occlusive coil 300 also includes an adapter 312 at least partially disposed in its lumen 306 at its proximal end 302. The adapter 312 depicted in FIG. 9 is an adapter coil having an open winding 318 its distal end. A stretch-resisting member 310, like the one depicted in FIG. 8, attaches the distal end 304 of the vaso-occlusive coil 300 to the open winding 318.

Figure 10:
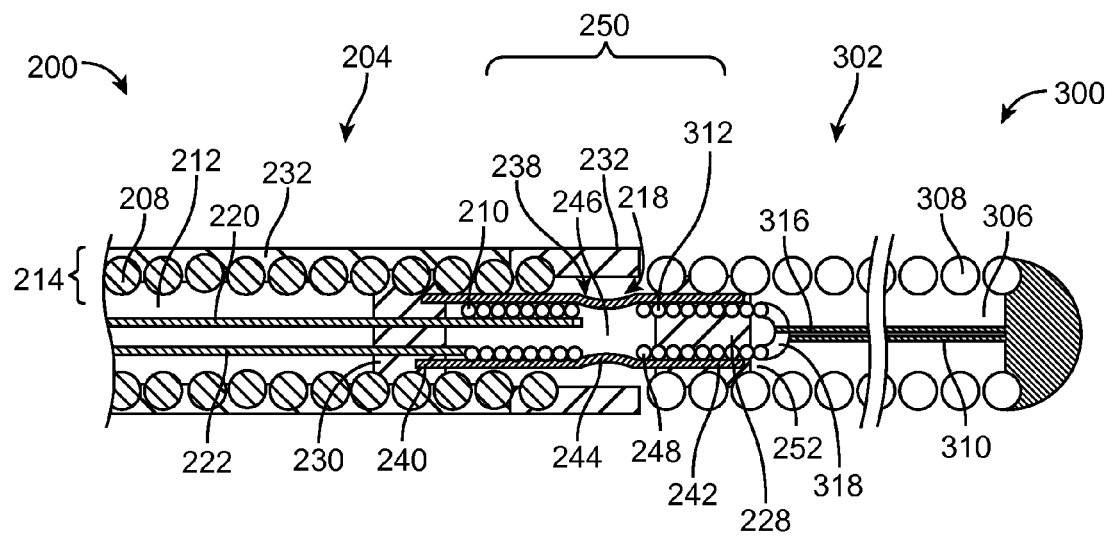

The vaso-occlusive device delivery system 10 depicted in FIG. 10 is similar to the systems 10 depicted in FIGS. 5 and 9. Similar elements of this embodiment are identified with the same reference numbers as discussed above with respect to FIGS. 5 and 9. Like the system 10 depicted in FIG. 5, the system 10 depicted in FIG. 10 has a modified detachment zone 244 and the addition of a locking coil 248. Like the system 10 depicted in FIG. 9, the outer sleeve 232 of the pusher assembly 200 depicted in FIG. 10 extends distally beyond the distal coil portion 208 of the pusher conduit 214, and the adapter 312 depicted in FIG. 10 is an adapter coil having an open winding 318 in its distal end. Also, a stretch-resisting member 310 attaches the distal end 304 of the vaso-occlusive coil 300 to the open winding 318. In the system 10 depicted in FIG. 10, the locking coil 248 and the adapter coil 312 are the same coil.

Figure 11:
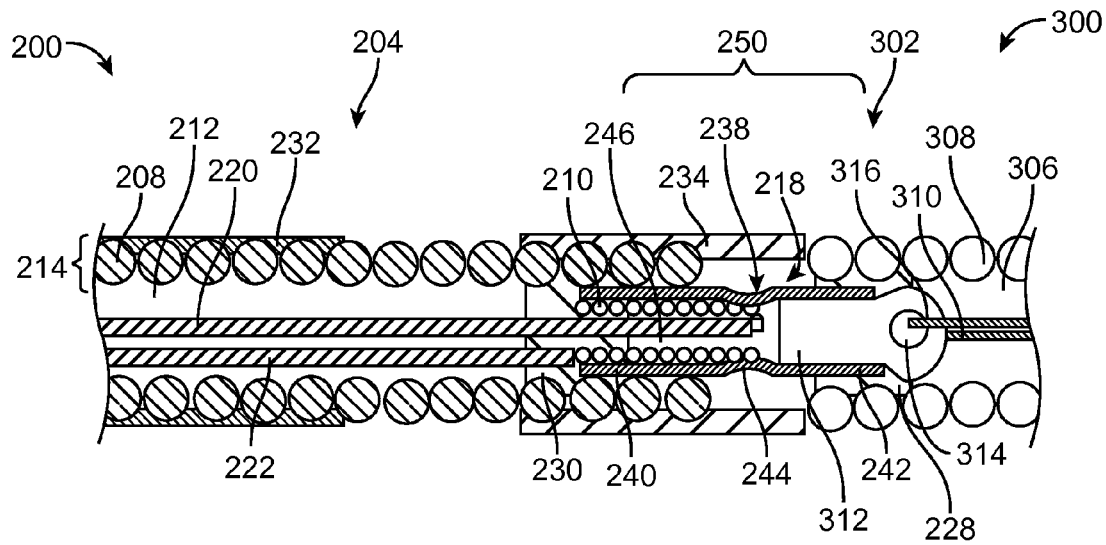

The vaso-occlusive device delivery system 10 depicted in FIG. 11 is similar to the systems 10 depicted in FIGS. 5 and 8. Similar elements of this embodiment are identified with the same reference numbers as discussed above with respect to FIGS. 5 and 8. Like the system 10 depicted in FIG. 5, the system 10 depicted in FIG. 11 has a modified detachment zone 244. Like the system 10 depicted in FIG. 8, the vaso-occlusive coil 300 includes a flattened adapter 312 at least partially disposed in its lumen 306 at its proximal end 302 having an opening 314 at its distal end. Also, a stretch-resisting member 310 attaches the distal end 304 of the vaso-occlusive coil 300 to the adapter 312. The adapter 312 is stamped from a platinum sheet for radiopacity. The outer sleeve 232 does not extend to the distal end 204 of the pusher assembly 200. Instead, a short PTFE tube 234 is laminated onto the distal end 204 of the pusher assembly 200, the detachment zone 244, and the proximal end of the adapter 312, which extends approximately of the vaso-occlusive coil 300.

Figure 12:
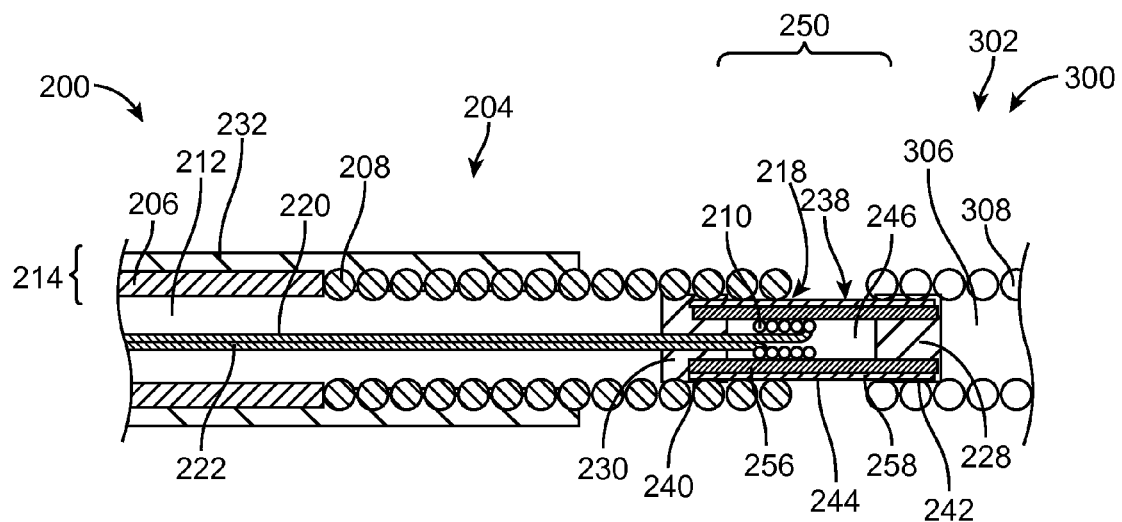

The vaso-occlusive device delivery system 10 depicted in FIG. 12 is also similar to the system 10 depicted in FIG. 3. Similar elements of this embodiment are identified with the same reference numbers as discussed above with respect to FIG. 3. The tubular member 238 depicted in FIG. 12 has a composite design including two layers, in this case, an inner tube 256 and an outer tube 258. In other embodiments, the two layers can be coextruded "bonded" layers of one tube. Each of the inner and outer tubes 256, 258 can be made from polymer, metal, alloy, or ceramic. The melting point of the inner tube 256 is preferably lower than that of the outer tube 258, and the inner tube 256 is preferably thicker than the outer tube 258. This composite tubular member 238 compliance the low melting point of the inner tube 256 with the structural strength of the outer tube 258. While the tubular member 238 depicted in FIG. 12 has two layers, the claims encompass tubular members having more than two layers.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A vaso-occlusive device delivery assembly, comprising:
    a pusher assembly having a proximal end, a distal end, and a pusher lumen extending therebetween;
    a vaso-occlusive device; and
    a tubular member mechanically connecting the pusher assembly to the vaso-occlusive device, the tubular member having a proximal end, a distal end, a tube lumen extending therebetween, and a detach zone,
    proximal and distal seals attached to, and forming respective seal with, the respective proximal and distal ends of the tubular member, such that the tubular member, proximal seal, and distal seal, collectively form a substantially fluid-tight chamber within the tube lumen,
    wherein the proximal end of the tubular member extends into the pusher assembly lumen at the distal end of the pusher assembly, and
    wherein a heat generating member is disposed in the tube lumen, such that, when activated, the heat generating member generates heat that melts or otherwise thermally degrades the tubular member at the detach zone, thereby detaching the vaso-occlusive device from the pusher assembly.

2. The vaso-occlusive device delivery assembly of claim 1, the pusher assembly further comprising first and second conductors extending between the proximal and distal ends of the pusher assembly,
    wherein the heat generating member is a resistive heater coil electrically connected to the respective first and second conductors to form an electrical circuit, and
    wherein the heat generating member is activated by applying a current therethrough.

3. The vaso-occlusive device delivery assembly of claim 2, wherein a pitch of a proximal portion of the heater coil is greater than a pitch of a distal portion of the heater coil, such that the heater coil has a non-uniform heat distribution.

4. The vaso-occlusive device delivery assembly of claim 1, wherein the detach zone is treated to accelerate detachment of the vaso-occlusive device from the pusher assembly.

5. The vaso-occlusive device delivery assembly of claim 4, wherein the detach zone is thermally weakened.

6. The vaso-occlusive device delivery assembly of claim 4, wherein the detach zone is mechanically weakened.

7. The vaso-occlusive device delivery assembly of claim 1, further comprising an elongate body disposed in the tube lumen at the distal end of the tubular member, wherein a distal portion of the tubular member is attached to an outer surface of the elongate body, thereby increasing a tension on the detach zone to accelerate detachment of the vaso-occlusive device from the pusher assembly.

8. The vaso-occlusive device delivery assembly of claim 1, further comprising a locking coil disposed in the tube lumen at the distal end of the tubular member, wherein both the locking coil and the distal end of the tubular member are disposed in a lumen of the vaso-occlusive device, the locking coil sized so as to increase an interference fit between the tubular member and the vaso-occlusive device.

9. The vaso-occlusive device delivery assembly of claim 1, wherein the pusher assembly further comprises a cylindrical body disposed around and thermally insulating the detach zone, and wherein the cylindrical body is configured to increase an axial columnar strength of the vaso-occlusive device delivery assembly.

10. The vaso-occlusive device delivery assembly of claim 1, wherein the tubular member comprises a radially enlarged distal portion, and wherein a proximal end of the vaso-occlusive device is secured to the tubular member by an interference fit within the radially enlarged distal portion of the tubular member.

11. The vaso-occlusive device delivery assembly of claim 1, wherein the proximal end of the tubular member is connected to the pusher assembly by a first adhesive connection and the distal end of the tubular member is connected to the vaso-occlusive device by a second adhesive connection.

12. The vaso-occlusive device delivery assembly of claim 2, wherein the first and second conductors extend through the proximal seal, and wherein the proximal seal maintains a substantially fluid-tight seal in the tube lumen.

13. The vaso-occlusive device delivery assembly of claim 1, the vaso-occlusive device comprising a stretch-resisting member having a distal end secured to a distal portion of the vaso-occlusive device, and a proximal end secured to an adapter disposed in a proximal end portion of a lumen of the vaso-occlusive device.

14. The vaso-occlusive device delivery assembly of claim 13, wherein the adapter comprises a flattened body defining an opening in the distal end thereof, and wherein the stretch-resisting member forms a loop passing through the opening, thereby attaching the stretch-resisting member to the adapter.

15. The vaso-occlusive device delivery assembly of claim 13, wherein the adapter comprises a coil, and wherein the stretch-resisting member forms a loop passing through an open winding in the distal end of the coil, thereby attaching the stretch-resisting member to the adapter.

16. The vaso-occlusive device delivery assembly of claim 1, wherein the heat generating member is configured to heat air within the pusher lumen to thereby increase a pressure therein to accelerate detachment of the vaso-occlusive device from the pusher assembly.

17. The vaso-occlusive device delivery assembly of claim 1, wherein the heat generating member comprises carbon.

18. The vaso-occlusive device delivery assembly of claim 1, wherein the tubular member comprises a polymer selected from the group consisting of high-density polyethylene, low-density polyethylene, polypropylene, polyethylene terephthalate, and polycaprolactone.

19. The vaso-occlusive device delivery assembly of claim 1, wherein the tubular member comprises a plurality of concentric layers, and wherein the tubular member comprises a low melting point inner layer and a high melting point outer layer.

* * * * *